United States Patent [19]

Sodhi

[11] Patent Number: 4,787,378
[45] Date of Patent: Nov. 29, 1988

[54] SELF-RETAINING NAIL FOR FRACTURE OF NECK OF FEMUR

[76] Inventor: Jitendra S. Sodhi, Manhattan Ville Station, Box 3227, New York, N.Y. 10027

[21] Appl. No.: 906,340

[22] Filed: Sep. 8, 1986

[51] Int. Cl.⁴ ............................................ A61M 37/00
[52] U.S. Cl. .......................... 128/92 YW; 128/92 YT; 128/92 YY; 128/92 YF
[58] Field of Search ....... 128/92 YW, 92 YT, 92 YY, 128/92 YF

[56] References Cited

U.S. PATENT DOCUMENTS

| | | | |
|---|---|---|---|
| 2,077,804 | 4/1937 | Morrison | 128/92 YW |
| 2,327,434 | 8/1943 | Johnston | 128/92 YW |
| 2,685,877 | 8/1954 | Dobelle | 128/92 YW |
| 3,216,414 | 11/1965 | Street | 128/92 YW |
| 4,236,512 | 12/1980 | Aginsky | 128/92 YW |
| 4,409,974 | 10/1983 | Freedland | 128/92 YF |

FOREIGN PATENT DOCUMENTS 2544918  5/1976  Fed. Rep. of Germany ........ 128/92 YY Primary Examiner—C. Fred Rosenbaum
Assistant Examiner—Colleen M. Reilly
Attorney, Agent, or Firm—Richard L. Miller

[57] ABSTRACT

The instant invention provides both a device and a method for treatment of a fractured neck of a femur. The device is such that it is inserted inside the broken femur and urges the two halves together so that the bone will unite and heal by natural growth processes. Unlike its predecessor the instant invention can be withdrawn from the femur once sufficient healing has taken place and the bone will continue to repair itself for all practical purposes to an extent as if no fracture had occurred.

8 Claims, 1 Drawing Sheet

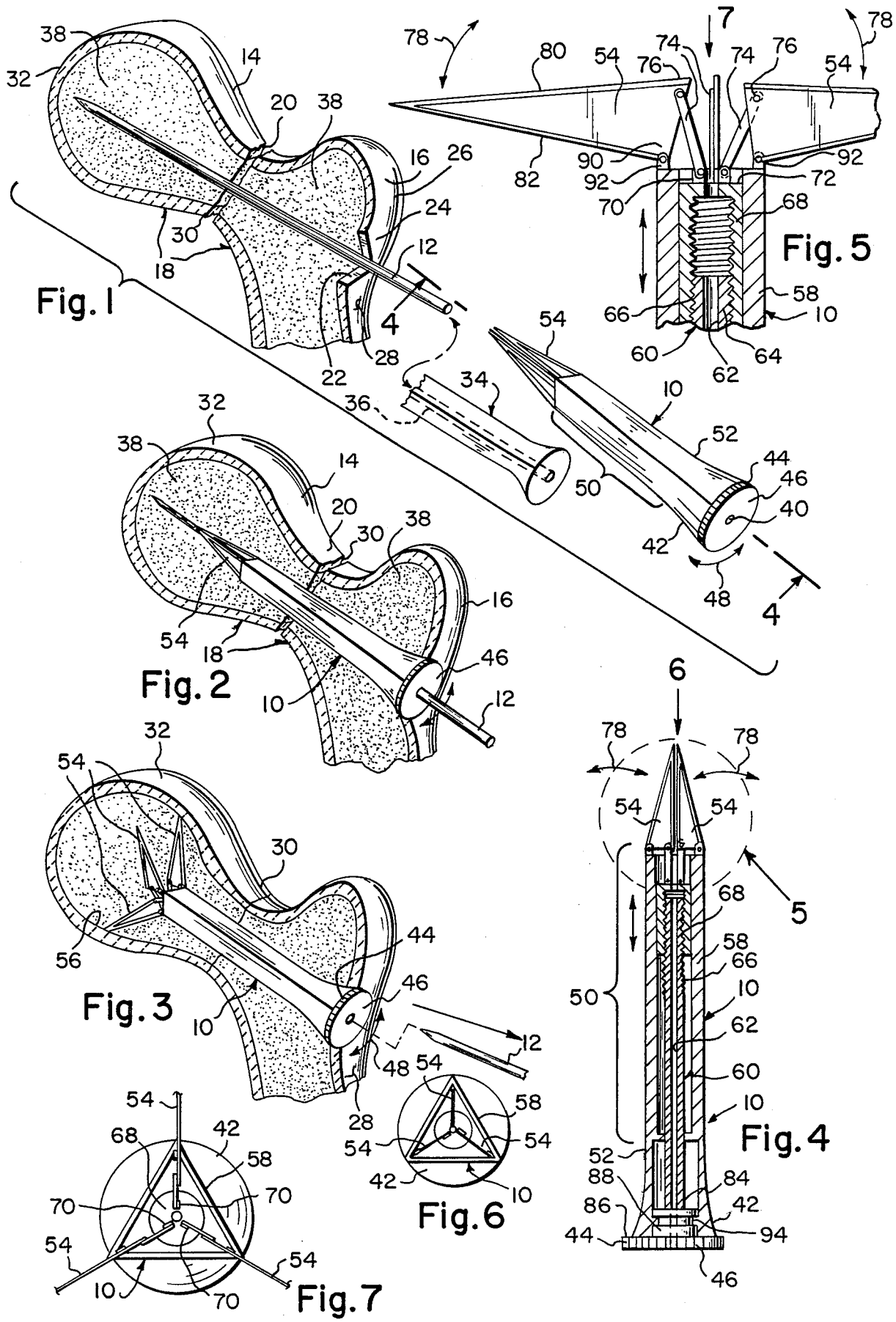

SELF-RETAINING NAIL FOR FRACTURE OF NECK OF FEMUR

BACKGROUND OF THE INVENTION

The instant invention relates generally to devices for treating fractures of the neck of the femur, and more specifically the devices which can be use to draw together a broken femur and hold it together until the bond can unite.

Numerous devices and jigs of different types have been provided in the prior art that are adapted to hold the fracture pieces of a broken femur in some sort of alignment until the bone can unite. For example, U.S. Pat. Nos. 2,077,804 to Morrison; 4,236,512 to Aginsky; and 4,519,100 to Wills all are illustrative of such prior art. While these units may be suitable for the particular purpose to which they address, they would not be as suitable for the purpose of the present invention as hereafter described.

SUMMARY OF THE INVENTION

A primary object of the present invention is to provide a self-retaining nail that will overcome the shortcomings of the prior art devices.

Another object is to provide a self-retaining nail that does not require a long incision in the patient as will be seen is the case when the device Aginsky (U.S. Pat. No. 4,236,512) is used.

An additional object is to provide a self-retaining nail that does not require that separate screws be placed in the femur causing more tissue trauma and increasing the possibility for more complication, and more discomfort for the patient.

A further object is to provide a self-retaining nail that cooperates with a system which prepares a passage in the damaged femur, and can then be used to guide or pilot the entry of the self retaining nail so that it will be inserted in the correct position with respect to the pieces of the broken femur.

A yet still further object is to provide a self-retaining nail that can be easily removed from the femur some time later, weeks, or even months, after the fracture pieces have had time to unite.

Yet still another object is to provide a self-retaining nail that is simple and easy to use.

A still further object is to provide self-retaining nail that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

FIG. 1 is a perspective cross sectional view of a fractured femur illustrating the instant invention about to be inserted in a opening provided therein.

FIG. 2 is a similar view to FIG. 1 after the instant invention has been inserted therein.

FIG. 3 is still another similar view to both figures 1 and 2 but illustrates the instant invention in the femur with blades spread apart so as to draw the fracture closed.

FIG. 4 is a cross sectional view taken along line 4—4 in FIG. 1 of just the instant invention per se illustrating the structure of the internal mechanism.

FIG. 5 is an enlarged detail view as indicated by arrow 5 in FIG. 4 of the tip portion but with the blades spread open.

FIG. 6 is an end view taken in the direction of arrow 6 in FIG. 4.

FIG. 7 is an enlarged view similar to FIG. 6, but with the blades spread open.

DETAILED DESCRIPTION OF THE PREFERRED EMBODIMENTS

Turning now descriptively to the drawings, in which like reference characters denote like elements throughout the several views, FIG. 1 shows the self-retaining nail 10 ready to be aligned with a guide skewer 12 which is already passed through a triangular opening 22 within the two pieces 14 and 16 of a broken femur 18 which has a fracture crack 20 the femur having been already prepared as described in the next paragraph to thus receive the self-retaining nail.

In order to properly prepare the femur 18 to receive the instant invention 10 the orthopedic surgeon must first pierce the femur 18 at the near end 24 close to the greater trochanter 26 which guide skewer 12. This is mostly easily accomplished by driving the sharp pointed end of skewer 12 through the outer surface 28 of the femur 18 with a small hammer (not shown), through the neck 30, the spongy bone tissue 38 inside thereof, and into the head 32 of the femur. A small punch 34 which has a coaxial passageway 36 is then aligned with the skewer 12 and also driven through the outer surface of the femur so as to punch a triangular opening 22 through the surface 28.

The skewer 12 serves as a pilot device first for the punch 34 and next for the self retaining nail 10 which also has a coaxial passageway 40 sized to cooperate with the skewer 12, so that the self-retaining nail will arrive at the desired correct position with in the femur 18.

As better seen in FIG. 2 the self-retaining nail has been placed over the skewer 12 and likewise driven through the triangular opening 22 after the punch 34 has been withdrawn.

The head end 42 of the self-retaining nail 10 has a disk member 46, with knurled serrations 44 upon an outer circumference thereof which may be rotated as indicated by arrow 48. The nail per se has a triangular cross sectional shape sized to just fit the opening 22 punched in femur 18, and thereby is prevented from rotating within the femur when the disk member 46 is rotated. The head end 42 of the self-retaining nail begins to flare at 52 to a slightly larger size then the majority of the shank portion 50, so that the fit becomes tight when the end is driven nearly flush with the surface 28 of femur 18.

Rotating the disk member 46 with respect to the rest of the device 10 per se causes three knife blade elements 54 to spread apart into an open position by a mechanism yet to be described. If the device is properly sized with respect to the femur 18 into which it has been installed these three blades 54 after cutting through the spongy bone tissue 38 in the femur will come to rest upon a somewhat hemispherical compacted bone surface 56 within the head portion of the fractured femur and force the fracture crack 20 to close as best seen in FIG. 3.

At this time the skewer 12 may be withdrawn while the self-retaining nail 10 can be left in place until the bone has united. After a sufficient length of time (weeks, or months) when the bone has set the disk member 46 is rotated in an opposite direction and the knife blade elements are caused to come back together cutting their way back through new spongy bone tissue which has filled in around the device during the ensuing time required for the bone to unite.

The entire device is now withdrawn from the newly united bone and in due course of time the triangular opening 22 will fill in with new bone tissue as will also the space that was occupied by the self-retaining nail itself.

A closer examination of FIGS. 4, 5, 6 and 7 reveals that the self-retaining nail 10 has a triangular cross sectional shaped outer housing 58 which has the majority of its length 50 uniform in dimension, and a portion toward the head end 42 which begins to gradually flare at 52 to a slight larger dimension. A tubular hollow shaft 60 has a through passageway 62 of such a diameter so as to loosely fit over the skewer 12 previously described. The end portion 64 of this shaft 60 has an external thread 66 which cooperates with an internally threaded piston 68, and forms a mechanism for adjusting the lateral position of piston 68 within the housing 58. When shaft 60 is rotated piston 68 which is caused to move laterally and moves three adjustment ears 70 which are integrally formed on the extreme end 72 thereof. Connecting links 74 which are pivotally attached at both ends between adjustment ears 70 and the inner corner ends 76 of knife blades elements 54, change their position with the movement of piston 68 and cause three knife blade elements 54 to either spread apart or come together as indicated by arrows 78 depending on the direction of rotation of shaft 60 and the responsive movement of piston 68. Similarly the outer corner ends 90 of blades 54 are pivotally attached to ears 92 rigidly mounted to housing 58.

Knife blades elements 54, are sharpened on both inner and outer edges 80 and 82 respectively so that they may easily cut through the spongy bone tissue 38 within the femur 18 as required and previously described during the insertion or removal of the instant invention 10 during an operation to repair the fractured neck 20. Even with aging, when the head of the femur becomes more hard within, the bilateral sharp tough blades 54 spread and close easily in the tough bone head 32 of femur 18.

A second end portion 84 of tubular hollow shaft 60 is fixedly attached to the disk member 46 which acts as an adjustment knob to allow the surgeon to spread the knife blades elements 54, after proper insertion of the device 10. This same disk member 46 allows the nail to be struck lightly with a hammer if required, and also acts as an excellent grasping device later when necessary to withdraw the nail, because it extends beyond the outer dimension of the head end 42 of housing 52, as best seen in FIG. 4, at 86. A grooved ferrule 88 is also fixedly attached to the tubular hollow shaft 60 and rotates therewith so as to permit the shaft 60 to rotate with respect to the housing 58 while preventing lateral movement of the shaft within the housing. A tang 94 or other similar part as well known in the art rides in the grove of ferrule 88 and thus permits the ferrule 88 to freely rotate but not laterally move within the housing 58.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A self-retaining nail intended for repairing a fractured neck of a femur comprising:
    (a) a housing;
    (b) a plurality of blades each sharpened on two opposite edges and rotatively mounted on said housing; and
    (c) means contained within said housing for adjusting the rotative position of said blades with respect to said housing after said self retaining nail has been inserted into said femur to be repaired, whereby said blades may cut through spongy bone tissue contained within said femur and draw the fracture neck of said femur together; wherein said nail has an axial passageway through its entire length which co-operates with a skewer so that said skewer may act as a pilot device for positioning said nail into a correct position in said femur, and wherein said nail has a regular polygon cross sectional shape so as to prevent said nail from rotating in a properly prepared opening in said femur.

2. A self-retaining nail intended for repairing a fractured neck of a femur as recited in claim 1, wherein said means contained within said housing for adjusting the rotative position of said blades with respect to said housing is a tubular shaft with a threaded end which cooperates with a piston having correspondingly mating threads.

3. A self-retaining nail intended for repairing a fractured neck of a femur as recited in claim 2, wherein said tubular shaft has fixedly attached thereto a disk member which extends beyond an outer dimension of said housing so as to permit easy grasping and rotating of said disk, whereby when said disk is rotated in a first direction said blades will spread apart and when said disk is rotated in a second direction said blades will come together.

4. A self-retaining nail intended for repairing a fractured neck of a femur as recited in claim 3, wherein said blades are mechanically coupled to said piston so as to spread apart and come together in response to the movement of said piston in said housing.

5. A self-retaining nail intended for repairing a fractured neck of a femur as recited in claim 4, wherein means are provided to permit said shaft to rotate freely in said housing while said same means prevent any longitudinal motion of said shaft with respect to said housing.

6. A self-retaining nail intended for repairing a fractured neck of a femur as recited in claim 1, wherein said regular polygon cross sectional shape is a triangle.

7. A method for repairing a fractured neck of a broken femur comprising:
    (a) piercing the surface near the greater trochanter of said femur with an appropriate guide skewer passing therethrough;
    (b) driving said skewer through said fractured neck and into the head portion of said broken femur;
    (c) aligning a cooperative punch over said skewer;

(d) guiding said cooperative punch through the surface of said femur and punching out a triangular shaped opening;
(e) withdrawing said cooperative punch;
(f) aligning a cooperative self-retaining nail over said skewer;
(g) guiding said cooperative self-retaining nail through the opening punched, out by said punch through said fractured neck, and into the head portion of said broken femur;
(h) withdrawing said appropriate guide skewer;
(i) causing blades attached to said self-retaining nail to spread apart, whereby said fractured in said neck of said broken femur is drawn together; and
(j) allowing sufficient time for the fracture to unite.

8. A method for repairing a fractured neck of a broken femur as recited in claim 7 further comprising the additional steps of:
(a) causing blades attached to said self-retaining nail to come back together; and then
(b) withdrawing said self-retaining nail from said femur.

* * * * *